United States Patent [19]

Lin

[11] Patent Number: 5,176,679

[45] Date of Patent: Jan. 5, 1993

[54] VERTEBRAL LOCKING AND RETRIEVING SYSTEM

[76] Inventor: Chih-I Lin, Fl. 3-1, No. 2, Lane 6, Szu Wei Road, Taipei, Taiwan

[21] Appl. No.: 764,222

[22] Filed: Sep. 23, 1991

[51] Int. Cl.$^5$ .............................................. A61F 17/53
[52] U.S. Cl. ........................................ 606/61; 606/59
[58] Field of Search ...................... 606/60, 61, 72, 73, 606/53, 59, 54

[56] References Cited

U.S. PATENT DOCUMENTS

| | | | |
|---|---|---|---|
| 4,611,580 | 9/1986 | Wu | 606/61 X |
| 4,771,767 | 9/1988 | Steffee | 606/61 X |
| 4,790,303 | 12/1988 | Steffee | 606/61 |
| 5,042,982 | 8/1991 | Harms et al. | 606/61 |
| 5,047,029 | 9/1991 | Aebi et al. | 606/61 |
| 5,053,034 | 10/1991 | Olerud | 606/61 |

Primary Examiner—Robert A. Hafer
Assistant Examiner—Sam Rimell
Attorney, Agent, or Firm—Bacon & Thomas

[57] ABSTRACT

A vertebral locking and retrieving system comprises at least one lock pin, a coupling component, a remedial component, and a plurality of locking components. The lock pin is composed of a threaded end portion and a receiving mount, which form therebetween a specified angle. The coupling component is connected at one end thereof to the receiving mount of the lock pin. The remedial component is secured at one end thereof to the deformed vertebra or to the upper vertebra or the lower vertebra immediately adjacent to the deformed vertebra and is connected at another end thereof to another end of the coupling component. The locking components are provided to fixedly fasten the lock pin and the remedial component with the coupling component.

10 Claims, 4 Drawing Sheets

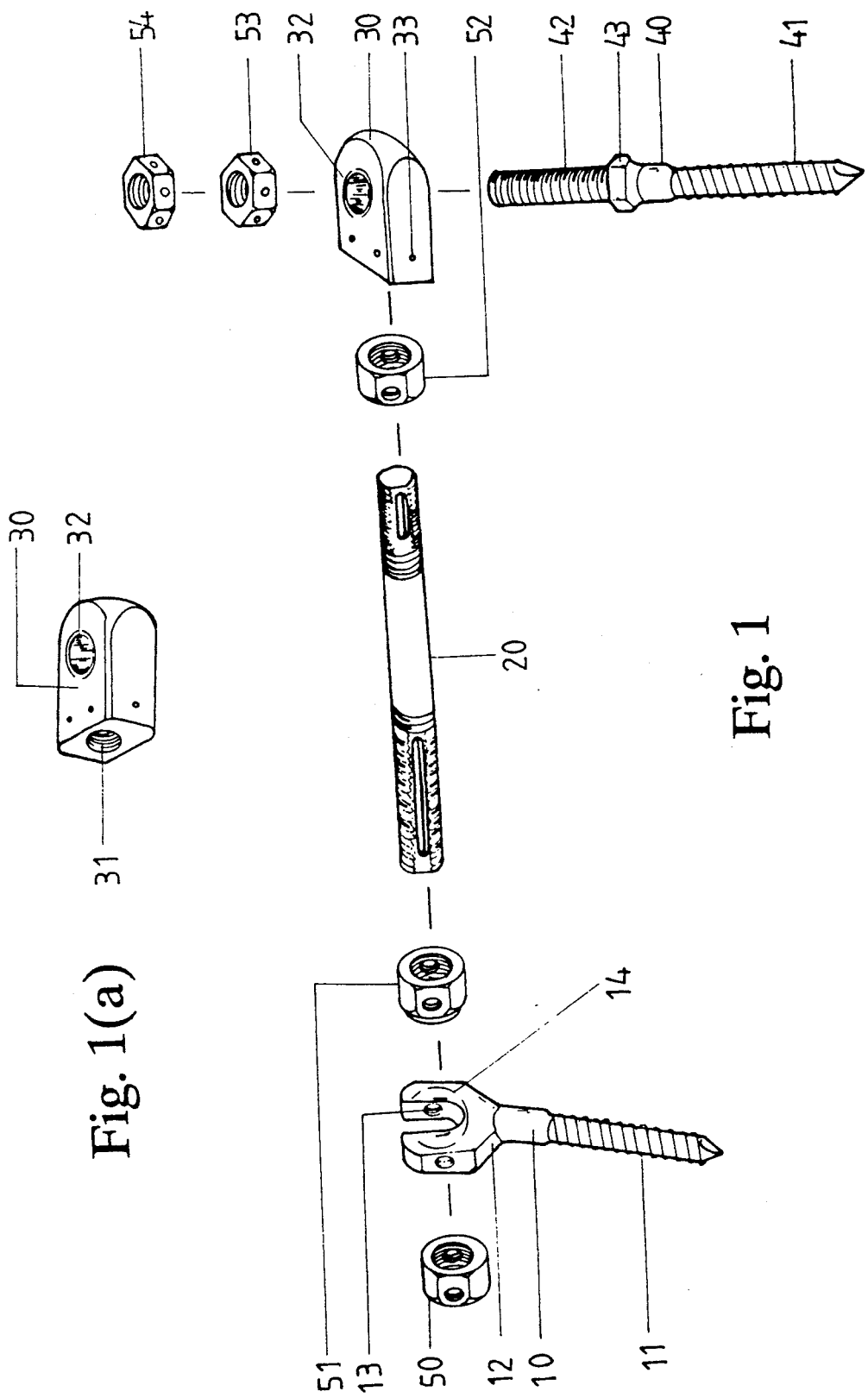

VERTEBRAL LOCKING AND RETRIEVING SYSTEM

BACKGROUND OF THE INVENTION

1. Field of the Invention

The present invention relates to a vertebral locking and retrieving system.

2. Description of the Prior Art

In general, conventional vertebral locking and retrieving systems of the prior art involve a locking process of multiple vertebrae, as exemplified by the LUGUE rod and the HARRINGTON rod, both made by Zimmer Company of U.S.A., and the ROY-CAMILLE plate produced by Howmedia Corporation of U.S.A. Such known prior art arrangements require a surgeon to make a large incision, which generally takes up too much of a surgeon's time and may bring about excessive bleeding by a patient receiving the treatment. The case in point is the LUGUE rod, which must be secured to two upper and lower vertebrae immediately adjacent to the injured or the deformed vertebra. This means that a surgeon is required to make a large incision to fix at least five segments of the spinal column. As a result, the patient's ability to move about is greatly hampered in the wake of such a surgical operation. In addition, the pressure exerting on the patient's nervous system by the locking and retrieving system of the prior art can not be effectively mitigated in view of the facts that the locking process is confined to a rear plate and that the retrieval of a front plate is not possible.

Furthermore, the surgical implantation of the conventional vertebral locking and retrieving systems of the prior art is further complicated by the fact that seven cervical vertebrae, twelve thoracic vertebrae, five lumbar vertebrae, and one caudal vertebra of the human spinal column differ in curvatures.

Other types of prior art vertebral locking and retrieving systems are disclosed respectively in U.S. Pat. Nos. 4,611,581 and 4,696,290. Such systems have also failed to deal with the surgical problems described above. In short, the existing vertebral locking and retrieving systems of the prior art have failed to address the surgical problems that are derived mainly from the fact that the curvatures of various vertebrae of the human spinal column are different from one another.

It is therefore the primary object of the present invention to provide a vertebral locking and retrieving system with locking pins which are designed in such unique manners that they have specific angles permitting the locking pins to cooperate with the specific curvatures of various vertebrae and that they serve to overcome the problems during and after the surgical operation having to do with locking multiple vertebrae.

It is another object of the present invention to provide a vertebral locking and retrieving system with means which can be used to lock two vertebrae of the spinal column.

It is still another object of the present invention to provide a vertebral locking and retrieving system with locking pins designed to have specific angles for correcting the position of various vertebrae having different curvatures.

SUMMARY OF THE INVENTION

In order to achieve the objects of the present invention, a vertebral locking and retrieving system comprising a lock pin, a coupling component, a remedial component, and a plurality of locking components is disclosed. The lock pin includes a threaded end portion adapted to be secured to a normal healthy vertebra and a receiving mount at its other end. The coupling component is connected at one end thereof to the receiving mount of the lock pin. The remedial component is secured at one end thereof to a deformed vertebra immediately adjacent to the healthy vertebra to which the locking pin is secured or a vertebra next to the deformed vertebra and different from this healthy vertebra and is connected at its other end thereof to the other end of the coupling component. The locking components enable the lock pin and the remedial component to be fixedly secured to the coupling component. Furthermore, the threaded end portion and the receiving mount of the lock pin are formed with a specified angle therebetween.

The receiving mount of the lock pin in the preferred embodiments of the present invention take the form of a fork, preferably a horseshoe-type structure, or a ring-type structure. Additional threaded holes, preferably two threaded holes, may be provided on both arms of the receiving fork so as to reinforce the connection between the lock pin and the coupling component by tightening screws into the threaded holes and against the coupling component.

The remedial component of the present invention may be a conventional screw, a laminar hook, or a lock pin with a specified angle. A plurality of remedial components may be used in combination with one coupling component of the present invention depending on the position and the symptom of the deformed vertebra and the surgical requirements.

In the preferred arrangement, the coupling components used in the present invention may include a single threaded rod or a plurality of threaded rods joined as a one-piece component by blocks having threaded bores into which the rods are received.

The foregoing features, objectives and advantages of the present invention will be better understood by studying the following detailed description of the preferred embodiments, in conjuction with the drawings provided herein.

BRIEF DESCRIPTION OF THE DRAWINGS

FIG. 1 shows an exploded perspective view illustrating a vertebral locking and retrieving system constructed according to one of the preferred embodiments of the present invention.

FIG. 1(a) shows an element of the vertebral locking and retrieving system of FIG. 1 in a different perspective view.

DETAILED DESCRIPTION OF THE PREFERRED EMBODIMENTS

Figure 2A:
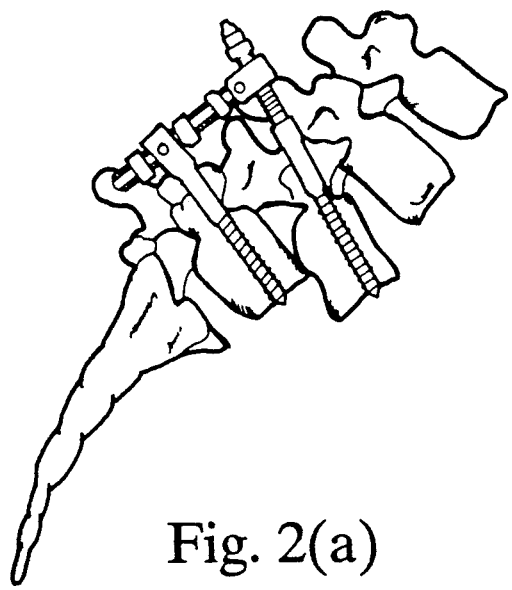
FIGS. 2(a)–2(c) show a series of correction procedures of a deformed vertebra by means of the vertebral locking and retrieving system shown in FIG. 1.

In general, the vertebral locking and retrieving system of the present invention can be made of orthopedic materials, such as the iron-based stainless steel 316LVM, the titanium-based material Ti-6-4, and an alloy of chromium, molybdenum and cobalt. The number of lock pins used is of course dependent on the surgical requirements. The lock pin of the present invention is characterized in that its receiving mount and its threaded end portion form a specified angle, such as 180°, 175°, 170°, or 165°, with a respective deflection plane angle being 0°, 5°, 10°, 15°, so as to meet the angular requirements of various vertebrae. Furthermore, with the employment of different combination of lock pins having the above-mentioned deflection plane angles of 0°, 5°, 10°, 15°, a slipped vertebrae can be properly retrieved to have an appropriate angle consistent with normal human anatomy, such as 0°, 5°, 10°, 15°, 20° (5°+15°), 25° (10°+15°), and 30° (15°+15°). This is something beyond the reach of the prior art systems. In addition, working with the prior art system, a surgeon would have to depend entirely on his or her own judgment and clinical experiences to determine the locking angle of the deformed vertebra. On the other hand, the present invention permits a surgeon to study in advance, before operating on the patient, the X-ray negatives with regard to the locking angles of the patient's vertebrae so as to select the most suitable lock pin to use.

Referring to FIG. 1, the vertebral locking and retrieving system embodied in the present invention is shown comprising mainly a lock pin 10, a threaded rod 20, a block 30, a remedial screw 40, and a plurality of nuts 50, 51, 52, 53, and 54. The lock pin is composed of a threaded end portion 11, a receiving horseshoe-type fork 12 having a recess 14 on each lateral side thereof, and screw holes 13. The threaded end portion 11 of the lock pin 10 is used to lock the normal vertebra immediately adjacent to the deformed vertebra under treatment. The block 30 is provided with a through hole 32, a plurality of small threaded holes 33, and a large threaded bore 31 (see FIG. 1(a)) used to engage with the threaded rod 20. The remedial screw 40 comprises a screw end 41 intended to be secured to the deformed vertebra, a threaded end 42 to be placed through the through hole 32 of the block 30, and a stopping protrusion 43, located between the screw end 41 and the threaded end 42, intended for use in stopping the block 30. The remedial screw 40 and the block 30 are components serving to correct and restore the deformed vertebra as will be discussed more fully below.

The nuts 50 and 51 are used to fixedly attach lock pin 10 to threaded rod 20, wherein the nuts 50, 51 are mounted on the screw rod 20 and threaded into recesses 14 of fork 12 separately when screw rod 20 extends through the slot defined by the horseshoe shape of fork 12. The nut 52 is driven against the block 30 to maintain the position of the block 30 on the threaded rod 20. The block 30 and the remedial screw 40 are fastened securely by means of nuts 53 and 54. If necessary, additional reinforcing screws (not shown) may be provided to secure the engagement between the lock pin 10 and threaded rod 20 by tightening the reinforcing screws into screw holes 13 of lock pin 10 and against the threaded rod 20.

Figure 2B:
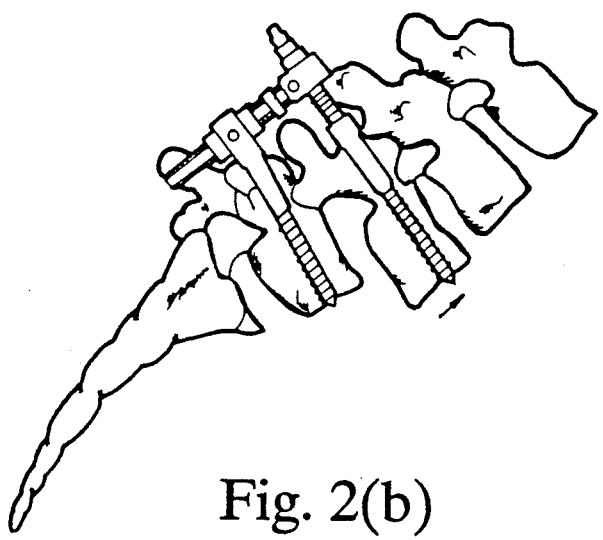
Figure 2C:
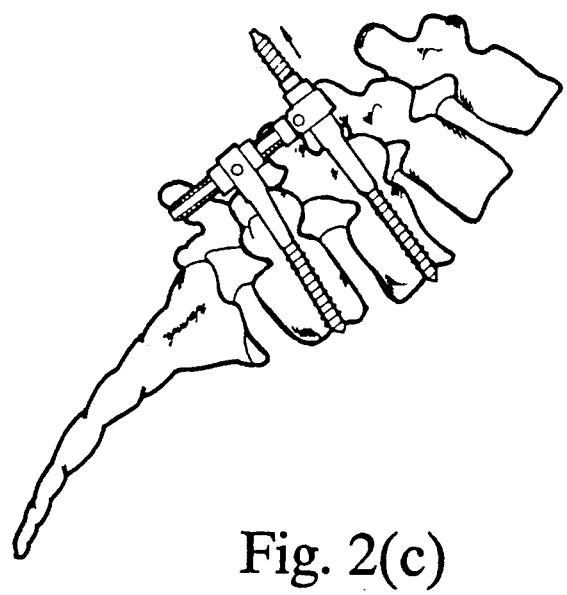

Now referring to FIG. 2(a), the fourth segment of the lumbar vertebrae is shown slipping from a normal, desired position prior to tightening of nuts 50 and 51 into the recesses 14 of locking pin 10. However, the slipped segment of the lumbar vertebrae is restored to its desired position of curvature relative to other normal and healthy segments of the lumber vertebrae as a result of the tightening action of nuts 50 and 51, as shown in FIG. 2(b). This is possible because the lock pin 10 is designed with a specified curvature (as discussed above) permitting the lock pin to negotiate and cooperate with a given segment of the lumber vertebrae. Now, as shown in FIG. 2(c), the nut 52 has been tightened against block 30 so as to restore a normal clearance between the slipped vertebra and the rest of the normal and healthy segments of the lumbar vertebrae. As nuts 53 and 54 are screwed respectively into their appropriate positions (i.e. from the FIG. 2(b) position to the FIG. 2(c) position), the slipped vertebra of the lumber vertebrae is retrieved to its normal position.

Figure 3:
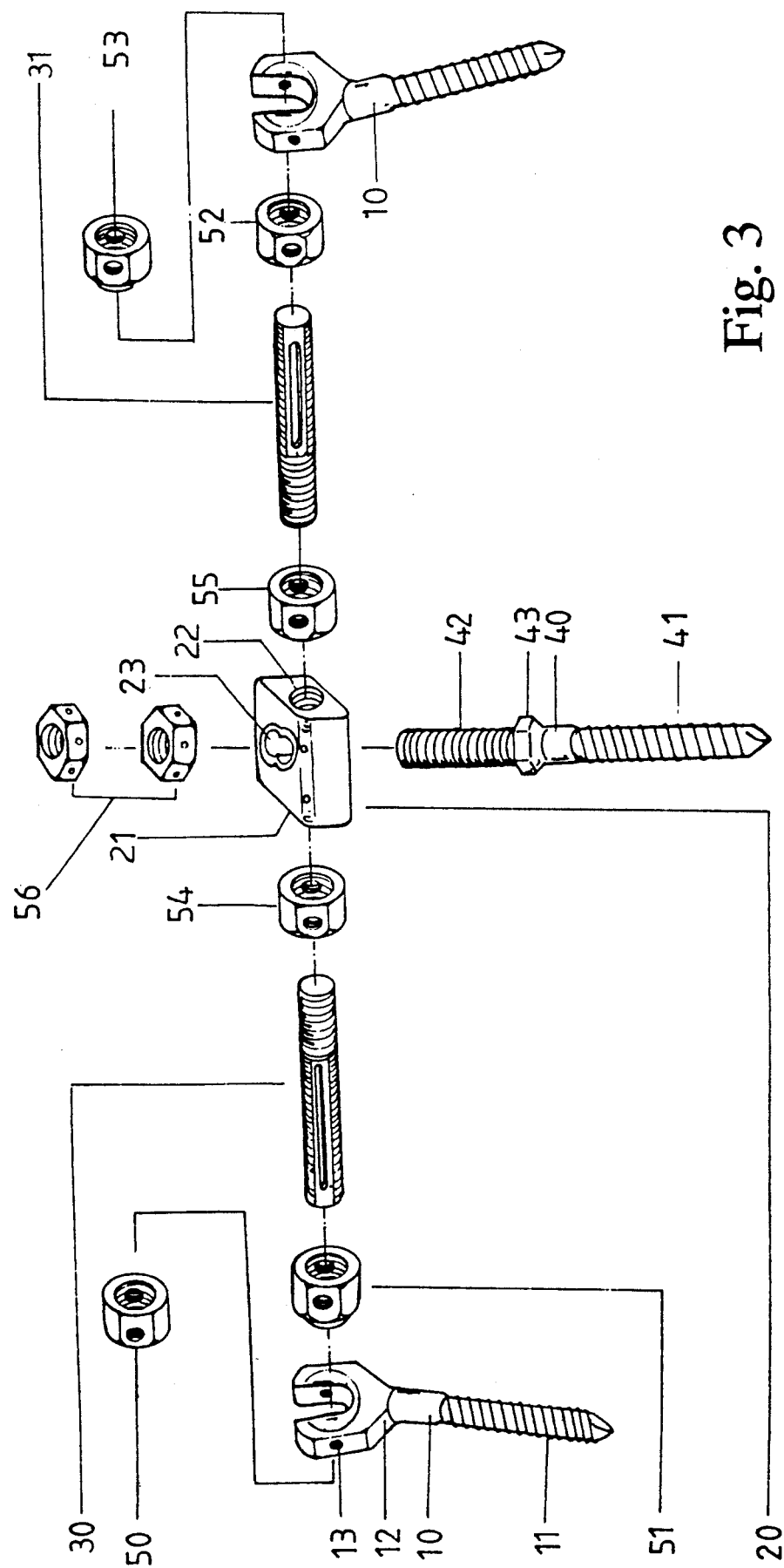
FIG. 3 shows an exploded perspective view of a vertebral locking and retrieving system constructed according to another preferred embodiment of the present invention.

Another preferred embodiment of the present invention is illustrated in FIG. 3 wherein like numerals are used to designate elements corresponding to the above described embodiment. The lock pin 10, which is composed of a threaded end 11, a receiving fork 12, and screw holes 13, is again used to secure the vertebrae immediately adjacent to the deformed vertebra. A connecting block 20 is provided with an 8-shape through hole 23 and threaded bores 22 and 21. Threaded rods 30 and 31 are threadably received within respective threaded bores 21 and 22 of block 20. The remedial screw 40 is intended to remedy the deformed vertebra and is similar in structure to the one shown in FIG. 1. In this embodiment, however, two lock pins 10 and two threaded rods 30 and 31 are fastened together to form a unitary body by means of nuts 50, 51, 52, and 53. The two threaded rods 30 and 31 and the fastening block 20 are fixedly secured together by threading nuts 54 and 55 against the block 20. In the meantime, the nuts 56 are used to couple the block 20 with the remedial screw 40 with the 8-shaped through hole 23 permitting a slight adjustment of remedial screw 40 relative to the axis defined by threaded rods 30, 31. The fastening block 20 and/or the threaded rods 30, 31 can be constructed with a specific angle for enabling the system to cooperate with the curvature of the deformed vertebra.

Figure 4C:
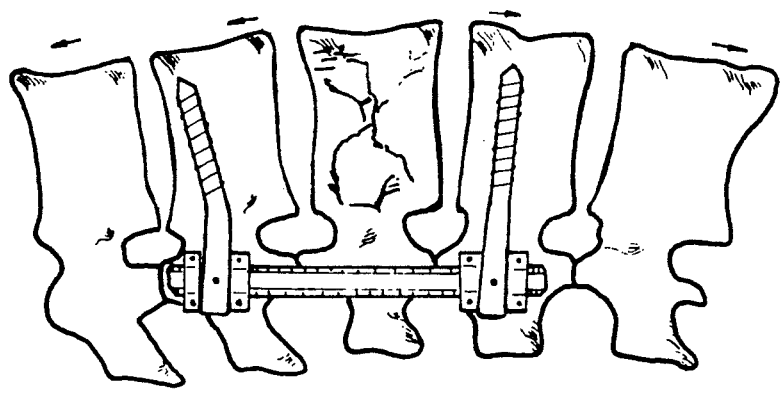
FIGS. 4(a)–4(c) show a series of correcting procedures of a deformed vertebra by means of a third preferred embodiment of the present invention.
Figure 4B:
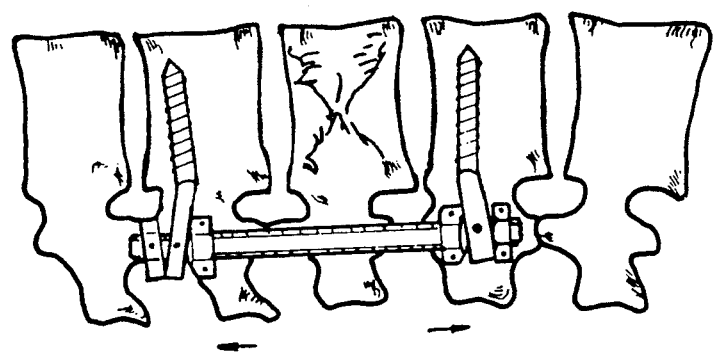
Figure 4A:
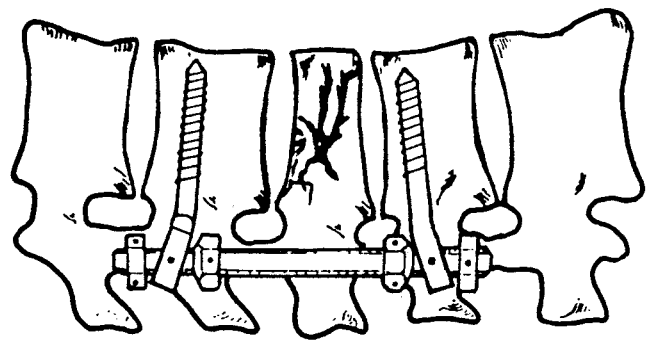

Now referring to FIGS. 4(a), 4(b) and 4(c), a third embodiment of the present invention is shown comprising two lock pins, one threaded rod as the coupling component and two sets of nuts. These components have not been labeled in FIGS. 4(a)-4(c), however, it should be clear that the structure is directly analogous to the connection of locking pins 10 to their respective threaded rods 20, 30 and 31 in the prior embodiments described. One of the lock pins is used to serve as a remedial component and is secured to the upper or the lower vertebra immediately adjacent to the deformed vertebra. In FIG. 4(a), the deformed vertebra is shown along with the present locking and retrieving embodiment implanted but which has not been securely fastened. In FIG. 4(b), the lock pins are secured to appropriate positions on the threaded rod as a result of tightening actions of two sets of nuts. Therefore, a lock pin with a specified angle is able to work to lock and retrieve the deformed vertebra. Upon completion of such treatment, all vertebrae in question have been restored to their respective normal positions, as shown in FIG. 4(c).

Based on the above discussion, it can readily be seen that the vertebral locking and retrieving system of the present invention is characterized in that it comprises lock pins, threaded rods, and nuts, all of which can be selectively employed in accordance with the position of the deformed vertebra, the symptoms of the deformed vertebra and the surgical requirements. For example, if the deformed vertebra happens to be the fourth vertebra of the lumbar vertebrae, the vertebral locking and retrieving system of the present invention shown in FIG. 1 functions effectively. In such a case, one threaded rod with the connecting block serves as the coupling component while a threaded screw is used as the remedial component. In addition, a plurality of nuts are used to work as locking components (see FIG. 1 and its corresponding text). In treating some slipped lumbar vertebrae, two threaded studs united by one connecting block are used as the coupling component for two lock pins and one threaded screw as in the FIG. 3 embodiment. In the case of vertebral fracture or camel back, one threaded rod may be used to serve as the coupling component to interconnect two lock pins, one of which is used to work as a remedial component (see FIGS. 4(a), 4(b) and 4(c), and the corresponding text).

In order to achieve a better surgical treatment, the present invention can also be employed in conjunction with numerous bone reinforcing devices known in the prior art, such as a cross bridging system.

From the above description, it can readily be seen that the present invention is characterized in that it comprises at least one lock pin which is designed with a specified angle enabling the lock pin to cooperate with the specific curvature of the deformed vertebra under treatment, and that its various components can be used in different combinations on the basis of the surgical requirements and the symptom of the deformed vertebra under treatment. Furthermore, the present invention serves to simplify the surgical operation in such ways that it does not require of a surgeon to make a large incision, thereby minimizing the risk of an excessive bleeding by the patient receiving treatment; the patient's ability to move about is not seriously compromised by the surgical operation; and the patient's nervous system is less vulnerable to the pressure exerted thereon by the implanted system.

The embodiments of the present invention described above are to be considered in all respects as merely illustrations of principles of the present invention. Accordingly, the present invention is to be limited only by the scope of the following claims.

I claim:

1. A vertebral locking and retrieving system for use in retrieving a deformed vertebra and maintaining the deformed vertebra in a normal, healthy position comprising:
   at least one locking pin having a threaded portion at one end thereof adapted to be secured to a normal, healthy vertebra and an integrally formed receiving mount at the other end thereof, said threaded portion defining a longitudinal axis, said receiving mount being formed at an acute angle of deflection relative to said axis;
   a remedial component adapted to be secured at one end thereof to one of a deformed vertebra located immediately adjacent to said normal, healthy vertebra or to a vertebra immediately adjacent to the deformed vertebra but different from said normal, healthy vertebra to which said at least one locking pin is secured;
   coupling means for interconnecting said at least one locking pin and said remedial component; and
   fastening means for fixedly securing said at least one locking pin and said remedial component to said coupling means.

2. A vertebral locking and retrieving system as claimed in claim 1, wherein said coupling means includes a rod having first and second threaded ends.

3. A vertebral locking and retrieving system as claimed in claim 2, wherein said receiving mount of said at least one locking pin is horseshoe-shaped thereby defining a slot through which said rod extends.

4. A vertebral locking and retrieving system as claimed in claim 3, wherein said fastening means includes a pair of nuts which are threadably attached to said rod on opposite sides of said receiving mount.

5. A vertebral locking and retrieving system as claimed in claim 4, wherein said receiving mount is formed with recesses about opposite lateral sides of said slot, said pair of nuts being tightened into said recesses.

6. A vertebral locking and retrieving system as claimed in claim 1, wherein said one end of said remedial component is threaded and the other end of said remedial component is connected to said coupling means.

7. A vertebral locking and retrieving system as claimed in claim 6, wherein said coupling means includes a rod having first and second threaded ends and a block, said first and second threaded ends of said rod being fixedly secured, by said fastening means, to said receiving mount of said at least one locking pin and said block respectively, the other end of said remedial component being fixedly secured to said block.

8. A vertebral locking and retrieving system as claimed in claim 7, wherein said remedial component includes a stop member formed intermediate the ends thereof, said block includes a hole through which the other end of said remedial component projects such that said block engages said stop member when said remedial component is fixedly secured to said block.

9. A vertebral locking and retrieving system as claimed in claim 8, wherein the other end of said remedial component is threaded and said fastening means comprises at least one nut which is threadably received on said other end of said remedial component such that said block is sandwiched between said at least one nut and said stop member.

10. A vertebral locking and retrieving system as claimed in claim 1, wherein said remedial component comprises a second locking pin.

* * * * *